United States Patent
Nitta et al.

(10) Patent No.: US 7,851,145 B2
(45) Date of Patent: Dec. 14, 2010

(54) NA+, K+-ATPASE EXPRESSION IN CERVICAL DYSPLASIA AND CANCER

(75) Inventors: Hiroaki Nitta, Oro Valley, AZ (US); Thomas M. Grogan, Tucson, AZ (US); Phillip Miller, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 197 days.

(21) Appl. No.: 12/096,075

(22) PCT Filed: Dec. 27, 2006

(86) PCT No.: PCT/US2006/049392

§ 371 (c)(1),
(2), (4) Date: Jun. 4, 2008

(87) PCT Pub. No.: WO2007/079128

PCT Pub. Date: Jul. 12, 2007

(65) Prior Publication Data

US 2008/0286386 A1 Nov. 20, 2008

Related U.S. Application Data

(60) Provisional application No. 60/755,223, filed on Dec. 30, 2005, provisional application No. 60/764,447, filed on Feb. 1, 2006.

(51) Int. Cl.
*C12Q 1/00* (2006.01)
(52) U.S. Cl. .......................................... 435/4; 435/7.23
(58) Field of Classification Search ...................... 435/4, 435/7.23
See application file for complete search history.

(56) References Cited

U.S. PATENT DOCUMENTS

| 6,221,623 | B1 | 4/2001 | Smith-McCune et al. |
| 6,380,167 | B1 | 4/2002 | Braude |
| 6,703,400 | B2 | 3/2004 | Johnson et al. |
| 6,922,586 | B2 | 7/2005 | Davies |
| 7,582,441 | B1 * | 9/2009 | Ruben et al. .............. 435/7.23 |
| 2003/0232350 | A1 | 12/2003 | Afar et al. |
| 2005/0129736 | A1 | 6/2005 | Hunter et al. |
| 2005/0282893 | A1 | 12/2005 | Au et al. |
| 2006/0135468 | A1 | 6/2006 | Khodadoust et al. |
| 2006/0172965 | A1 | 8/2006 | Shepard et al. |
| 2006/0205679 | A1 | 9/2006 | Streeper et al. |
| 2006/0234970 | A1 | 10/2006 | Jimenez et al. |

FOREIGN PATENT DOCUMENTS

| WO | WO 98/41648 A2 | 9/1998 |
| WO | WO 01/82910 A2 | 11/2001 |
| WO | WO 03/086292 A2 | 10/2003 |
| WO | WO 2005/060951 A2 * | 7/2005 |

OTHER PUBLICATIONS

Barwe et al., "Novel Role for Na,K-ATPase in Phosphatidylinositol 3-Kinase Signaling and Suppression of Cell Motility," *Mol. Biol. Cell* 16:1082-1094, 2005.

Johnson, et al., "Multiplex Gene Expression Analysis for High-Throughput Drug Discovery: Screening and Analysis of Compounds Affecting Genes Overexpressed in Cancer Cells," *Mol. Can. Ther.* 1:1293-1304, 2002.

Kolanjiappan et al., "Measurement of Erythrocyte Lipds, Lipid Peroxidation, Antioxidants and Osmotic Fragility in Cervical Cancer Patients," *Clin. Chim. Acta* 326:143-149, 2002.

Moxnes and Hausken, "Predicting the Concentration Level of an Anti-Cancer Drug During Treatment of a Living Organism," *Med. Hypotheses* 60:498-500, 2003.

Weidemann, "Na/K-ATPase Endogenous Digitalis-Like Compounds and Cancer Development—A Hypothesis," *Front. Biosci.* 10:2165-2176, 2005.

* cited by examiner

*Primary Examiner*—Ralph Gitomer
(74) *Attorney, Agent, or Firm*—Klarquist Sparkman, LLP

(57) ABSTRACT

The present disclosure provides methods of diagnosing cervical dysplasia and cervical cancer by detecting $Na^+$, $K^+$-ATPase expression. For example, it is demonstrated herein that expression of the $Na^+$, $K^+$-ATPase $\beta1$-subunit increases in cervical dysplasia and cervical cancer, relative to normal cervical tissue. Also provided are methods of treating cervical dysplasia and cervical cancer by decreasing the biological activity of the $Na^+$, $K^+$-ATPase. For example, therapeutically effective amounts of one or more $Na^+$, $K^+$-ATPase inhibitors can be applied to the cervix to treat cervical dysplasia and cervical cancer.

24 Claims, 3 Drawing Sheets

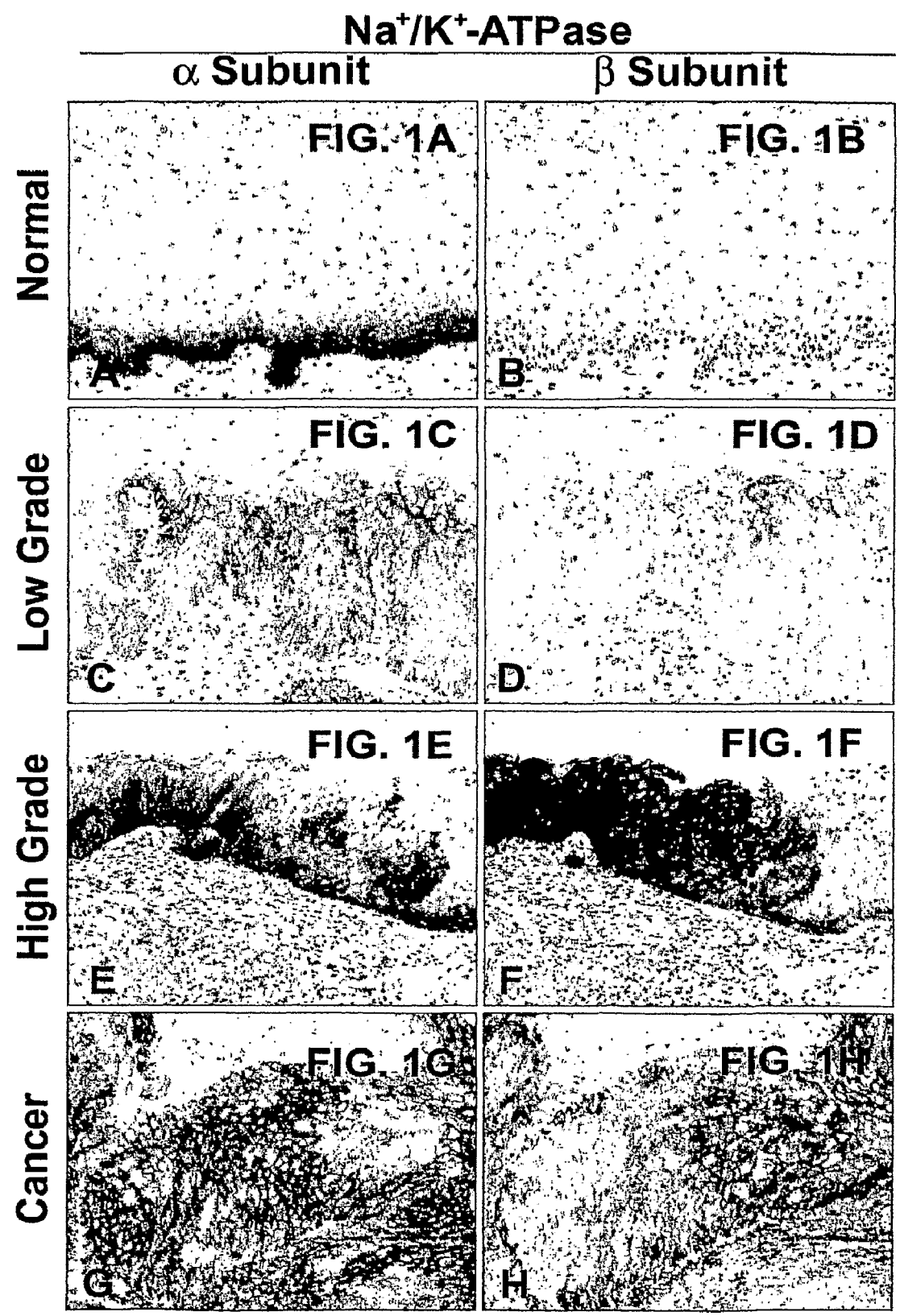

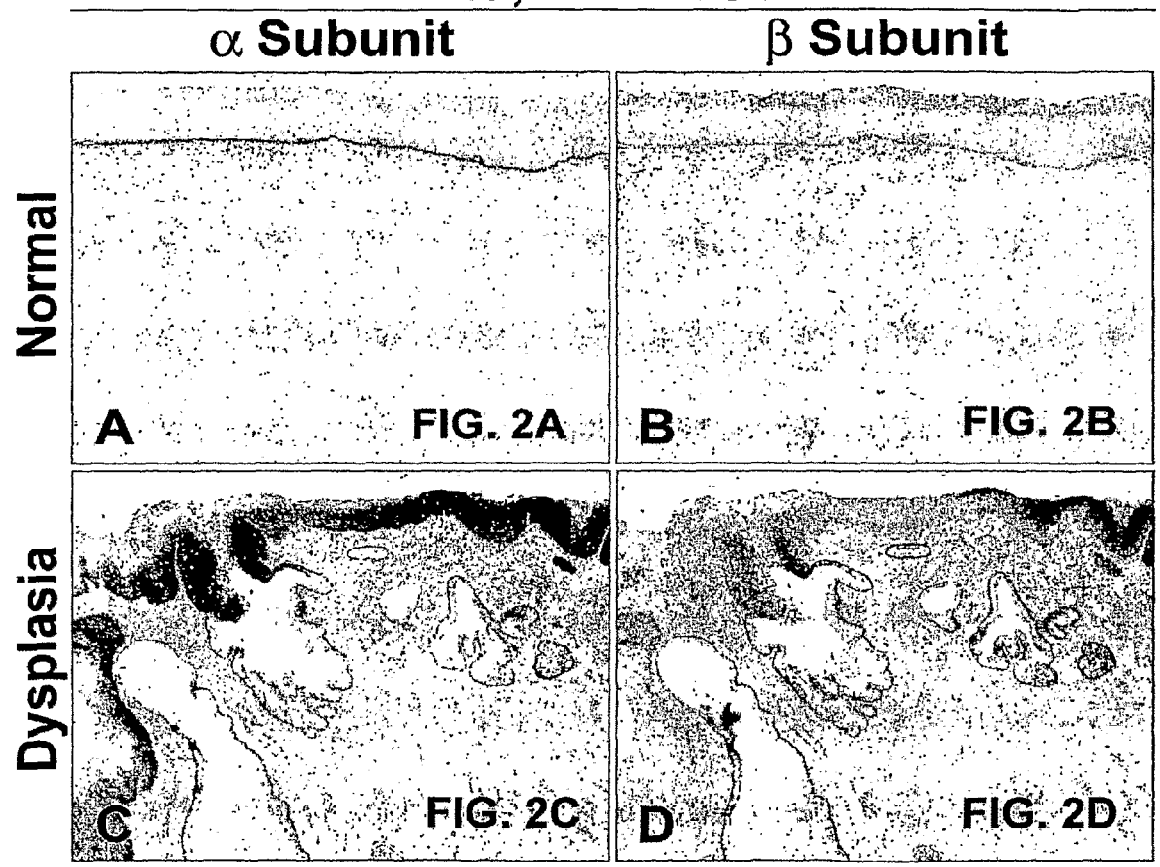

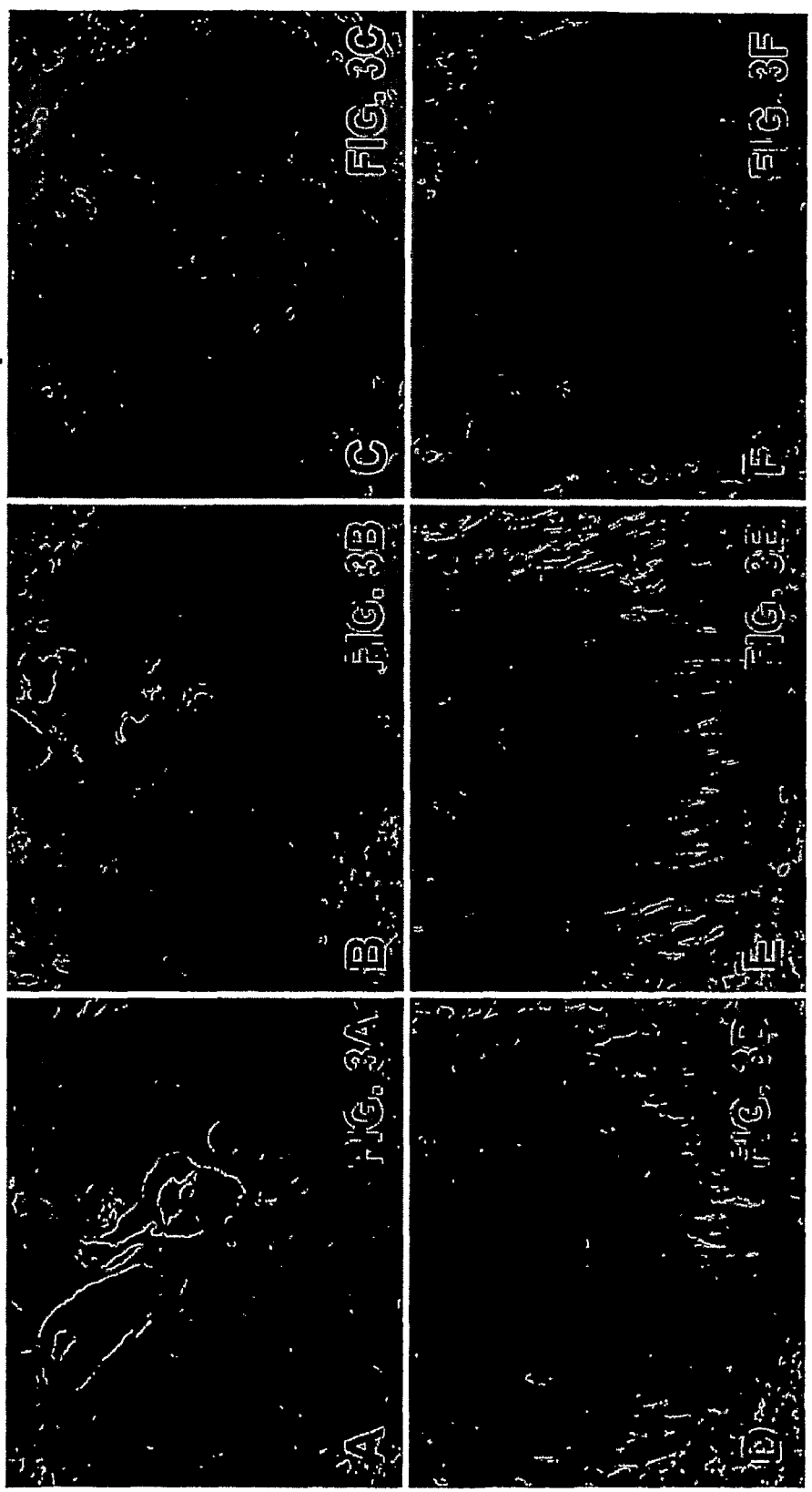

NA$^+$, K$^+$-ATPASE EXPRESSION IN CERVICAL DYSPLASIA AND CANCER

CROSS REFERENCE TO RELATED APPLICATIONS

This is the U.S. National Stage of International Application No. PCT/US2006/049392, filed Dec. 27, 2006 (published in English under PCT Article 21(2)), which claims the benefit of U.S. Provisional Application No. 60/764,447 filed Feb. 1, 2006 and U.S. Provisional Application No. 60/755,223 filed Dec. 30, 2005, both herein incorporated by reference.

FIELD

This application relates to methods of diagnosing cervical dysplasia and cancer by detecting Na$^+$, K$^+$-ATPase expression, and to methods of treating cervical dysplasia and cancer by decreasing the biological activity of the Na$^+$, K$^+$-ATPase.

BACKGROUND

The goal of cervical cancer prevention is to detect and treat all "committed" pre-cancer cells before the invasion of cancer cells occurs. Human papillomavirus (HPV) is a factor for the development of cervical cancer, and its detection in cervical tissue is currently used to diagnose cervical dysplasias and cancers. However, most HPV-induced lesions are cleared by the patient's natural immune system and only a small portion of women with HPV infected cervix actually develop cervical cancer. Therefore, biomarkers are needed that facilitate detection of the group of pre-cancer cells among low and high grade clinical cases and all cancer cases. Once biomarkers for the early detection of cervical cancer are identified, those biomarkers become are candidates for the treatment of cervical dysplasia.

SUMMARY

The inventors have determined that Na$^+$, K$^+$-ATPase expression in cervical tissue, such as the level of β1-subunit expression and the relative expression of the α-and β1-subunits, differs in normal cervical tissue as compared to cervical dysplasia and cervical cancer tissue. For example, increased expression of the Na$^+$, K$^+$-ATPase β-subunit in cervical tissue correlates with progression from low grade dysplasia to high grade dysplasia to cervical cancer. In addition, the ratio of expression of the Na$^+$, K$^+$-ATPase α-subunit to the β-subunit in cervical tissue decreased with progression from low grade dysplasia to high grade dysplasia to cervical cancer. The localization pattern of Na$^+$, K$^+$-ATPase differed in normal and diseased cervical tissue. In some examples, normal Na$^+$, K$^+$-ATPase expression was basal, while in cervical dysplasia or cancer tissue Na$^+$, K$^+$-ATPase expression was more localized to the cell membrane. Based on these observations, methods are provided for using the Na$^+$, K$^+$-ATPase as a biomarker for cervical dysplasia and cervical cancer and as a therapeutic target for treatment of cervical dysplasia and cancer.

Methods are provided for detecting cervical dysplasia or cervical cancer in a subject. In particular examples, the method includes detecting Na$^+$, K$^+$-ATPase expression (such as protein or nucleic acid molecule expression) in a cervical sample obtained from the subject For example, expression of the β-subunit (such as the β1-subunit), the α-subunit, or both, can be detected. In particular examples, the expression levels are quantitated. For example, the detected Na$^+$, K$^+$-ATPase expression can be compared to a reference value or reference sample representing a particular disease state (such as cervical dysplasia or cervical cancer, or a particular stage thereof). For example, the detected level of Na$^+$, K$^+$-ATPase expression in the sample can be compared to a level of Na$^+$, K$^+$-ATPase expression in one or more reference cervical tissue samples or to a reference value representing expected Na$^+$, K$^+$-ATPase expression in a control tissue sample. Exemplary reference samples and values include those representing a known presence, absence, or grade of cervical dysplasia or cervical cancer. For example, if the detected level of Na$^+$, K$^+$-ATPase expression (such as expression of the β subunit) is substantially similar to the level of Na$^+$, K$^+$-ATPase expression (such as expression of the β subunit) in a particular reference sample or value, this indicates that the subject has that presence, absence or grade of cervical dysplasia or cervical cancer represented by the reference sample or value. In a specific example, if the reference value or sample is normal (non-dysplastic, non-cancerous) cervical cells, a detected increase in Na$^+$, K$^+$-ATPase expression of at least 2-fold (such as at least 3-fold) relative to such a reference value indicates the presence of cervical dysplasia or cervical cancer in the cervical sample obtained from the subject.

The disclosed method can further include detecting α-subunit of a Na$^+$, K$^+$-ATPase expression in a cervical tissue sample and determining the ratio of the α- and β-subunit expression. In some examples, the determined ratio is compared to a ratio of α- and β-subunit expression observed in one or more reference values or samples having a known presence, absence or grade of cervical dysplasia or cervical cancer. For example, if the detected ratio of α- and β-subunit expression is substantially similar to the ratio of α- and β-subunit expression in a particular reference sample or value, this indicates that the subject has that presence, absence or grade of cervical dysplasia or cervical cancer represented by the reference sample or value. In a specific example, if the reference value or sample is normal (non-dysplastic, non-cancerous) cervical cells, a detected decrease in the ratio of α- and β-subunit expression (such as a decrease of at least 20% or at least 50%) relative to such a reference value indicates the presence of cervical dysplasia or cervical cancer in the cervical sample obtained from the subject.

In some examples, the disclosed methods can further include detecting another marker, such as a cell cycle marker, for example a nuclear marker. For example, the method can include detecting histone H3 (for example using histone H3-specific antibodies). Such additional markers can be used to further distinguish normal cervical tissue from cervical dysplasia or cervical cancer. For example, an increase in detected dividing cells-relative to normal cervical tissue (such as an increase of at least 2-fold, at least 5-fold, or at least 10-fold, such as 2-3 fold, 2-10 fold, or 2-20 fold) would indicate the presence of cervical dysplasia or cervical cancer.

The method of detecting and grading cervical dysplasia or cervical cancer can also include determining the localization pattern of the Na$^+$, K$^+$-ATPase (such as the α- or β-subunit) in a cervical sample. The location of either or both of the α- or β-subunits in a cervical tissue sample can be compared to one or more reference values or samples having a known presence, absence or grade of cervical dysplasia or cervical cancer. For example, if the detected Na$^+$, K$^+$-ATPase localization is substantially similar to the Na$^+$, K$^+$-ATPase localization in a particular reference sample or value, this indicates that the subject has that presence, absence or grade of cervical dysplasia or cervical cancer represented by the reference sample or value. In a specific example, if the reference value or sample is normal (non-dysplastic, non-cancerous) cervical cells, a detected Na$^+$, K$^+$-ATPase localization (such as increased localization in the cell membrane) relative to such a reference value indicates the presence of cervical dysplasia or cervical cancer in the cervical sample obtained from the subject.

The present disclosure also provides therapeutic compositions. In one example, such compositions include one or more Na$^+$, K$^+$-ATPase inhibitors (such as an inhibitor of the β-subunit) and a pharmaceutically acceptable carrier. In one example, the pharmaceutically acceptable is a carrier that permits topical application of the Na$^+$, K$^+$-ATPase inhibitor, for example topical application to the cervix. Na$^+$, K$^+$-ATPase inhibitors can significantly decrease the enzymatic activity of the protein (such as a cardiac glycoside) or decrease expression of a Na$^+$, K$^+$-ATPase (such as an inhibitory RNA molecule).

Methods are also provided for treating cervical dysplasia and cervical cancer. In one example, the method includes administering to a subject having cervical dysplasia or cervical cancer a composition that includes a therapeutically effective amount of a Na$^+$, K$^+$-ATPase inhibitor, such as a composition provided herein. For example, a subject determined to have cervical dysplasia or cervical cancer using the methods described herein can be selected to receive treatment for the cervical dysplasia. In some examples, the diseased cervix can be contacted with a Na$^+$, K$^+$-ATPase inhibitor in an amount and for a time sufficient to lower Na$^+$, K$^+$-ATPase activity in the cervix (for example in the cervical dysplastic or cancer cells).

The foregoing and other objects and features of the disclosure will become more apparent from the following detailed description, which proceeds with reference to the accompanying figures.

BRIEF DESCRIPTION OF THE DRAWINGS

FIGS. 1A-H show digital images of the immunolocalization of Na$^+$, K$^+$-ATPase (A, C, E, G) α and (B, D, F, H) β subunits in (A, B) normal cervical tissue, (C, D) low grade cervical dysplasia, (E, F) high grade cervical dysplasia, and (G, H) cervical cancer tissue samples. Normal cervical tissue expressed the Na$^+$, K$^+$-ATPase α subunit, but not the β1 subunit. Cervical dysplasia and cervical cancer samples were positive for both the Na$^+$, K$^+$-ATPase α and β1 subunits.

FIGS. 2A-D show digital images of cervical tissue stained to reveal Na$^+$, K$^+$-ATPase expression in endocervical mucus glands. The endocervical mucus glands are rarely seen in (A and B) normal samples and are mainly observed in the stroma of (C and D) cervical dyplasia samples.

FIGS. 3A-F show digital images comparing (A and D) centromere and (B and E) telomere in situ hybridization with (C and F) Na$^+$, K$^+$-ATPase β-subunit levels in cervical dysplasia tissue samples. These figures demonstrate that in cases of cervical dysplasia, the increased level of Na$^+$, K$^+$-ATPase β-subunit correlates positively with telomere shortening (indicated by a low level of staining in E).

DETAILED DESCRIPTION

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a Na$^+$, K$^+$-ATPase inhibitor" includes single or plural Na$^+$, K$^+$-ATPase inhibitors and is considered equivalent to the phrase "comprising at least one Na$^+$, K$^+$-ATPase inhibitor." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs.

HPV: human papillomavirus

Na$^+$, K$^+$-ATPase: sodium potassium ATPase (also referred to as the sodium pump)

Administration: To provide or give a subject an agent, such as a composition that includes a Na$^+$, K$^+$-ATPase inhibitor, by any effective route. Exemplary routes of administration include, but are not limited to, oral, injection (such as subcutaneous, intramuscular, intradermal, intraperitoneal, and intravenous), sublingual, rectal, transdermal, intranasal, vaginal, cervical, and inhalation routes. In specific examples, administration of an agent is accomplished via vaginal or cervical administration.

Antibody: A molecule including an antigen binding site which specifically binds (immunoreacts with) an antigen. Includes immunoglobulin molecules and immunologically active portions thereof, as well as immunoglobulin-like molecules. Immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. In particular examples, a Na$^+$, K$^+$-ATPase-specific antibody is used to detect expression or localization of the Na$^+$, K$^+$-ATPase in a cell. Antibodies include both monoclonal and polyclonal antibody preparations.

In some examples, an antibody specifically binds to a target (such as a Na$^+$, K$^+$-ATPase) with a binding constant that is at least $10^3$ M$^{-1}$ greater, $10^4$ M$^{-1}$ greater or $10^5$ M$^{-1}$ greater than a binding constant for other molecules in a sample. In other examples, an antibody has a Kd value for binding to an antigenic determinant (such as a hapten or epitope) that is on the order of $10^{-6}$ M or lower, such as $10^{-9}$ M or lower, or even $10^{-12}$ M or lower. Kd values can, for example, be determined by competitive ELISA (enzyme-linked immunosorbent assay) or using a surface-plasmon resonance device such as the Biacore T100, which is available from Biacore, Inc., Piscataway, N.J.

Antibody fragments include proteolytic antibody fragments [such as F(ab')2 fragments, Fab' fragments, Fab'-SH fragments and Fab fragments], recombinant antibody fragments (such as sFv fragments, dsFv fragments, bispecific sFv fragments, bispecific dsFv fragments, diabodies, and triabodies), camelid antibodies (see, for example, U.S. Pat. Nos. 6,015,695; 6,005,079; 5,874,541; 5,840,526; 5,800,988; and 5,759,808), and antibodies produced by cartilaginous and bony fishes and isolated binding domains thereof (see, for example, International Patent Application No. WO03014161).

Cardiac glycoside: An inhibitor of the Na$^+$, K$^+$-ATPase, which is traditionally used to treat congestive heart failure and cardiac arrhythmia. Such glycosides are found as secondary metabolites in several plants, and in some animals. For example, cardiac glycosides can be obtained from *Strophan-*

*thus* (such as ouabain g/k/e-strophanthin), *Digitalis lanata* and *Digitalis purpurea* (digoxin, digitoxin), *Scilla maritima* (proscillaridine A), *Adonis vernalis, Adonis aestivalis, Acokanthera oblongifolia, Convallaria*, and frogs (such as bufalin, marinobufagenin and bufadienolides). Additional non-limiting examples are provided in US Patent Publication 20060205679.

Cervical cancer: A malignant neoplasm of the cervix that has undergone characteristic anaplasia with loss of differentiation, increased rate of growth, invasion of surrounding tissue, and is capable of metastasis. There are two main types of cervical cancer: squamous cell (epidermoid) cervical cancer and adenocarcinoma cervical cancer. In particular examples, cervical cancer is caused by infection with human papillomavirus (HPV). Cervical cancer can be classified by the degree of spread of cancer cells, with stage I the least severe and stage IV the most severe (for example metastazied).

Cervical dysplasia (cervical intraepithelial neoplasia (CIN)): The presence of abnormal cells (cells which have not matured) on the cervix. Dysplasias are considered precancerous. The more abnormal cells found on the surface, the more serious the dysplasia. Cervical dysplasia is often classified by the degree of penetration of abnormal cells into the tissue lining (epithelium): CIN I describes the involvement of the basal third of the epithelium; CIN II involves the basal two thirds of the epithelium; and CIN III involves more than two thirds of the epithelium. When the entire cervical epithelium (the tissue that lines the cervix) is covered with primitive cells, this is referred to as cervical carcinoma in situ.

Cervical sample: A biological specimen obtained from the cervix, which can include cells from both the outside of the cervix (exocervix, or portio) and the inside of the cervix (endocervix). Exemplary methods that can be used to obtain a cervical sample include a PAP smear, colposcopy, and cone biopsy.

Cervix: The lower part of the uterus that opens into the vagina.

Chemotherapy: In cancer treatment, such as treatment of cervical cancer, chemotherapy refers to the administration of one or more agents to kill or slow the reproduction of rapidly multiplying cells, such as tumor or cancer cells. In a particular example, chemotherapy refers to the administration of one or more anti-neoplastic agents to significantly reduce the number of tumor cells in the subject, such as a reduction of at least 10%, at least 20%, or at least 50%. Cytotoxic anti-neoplastic chemotherapeutic agents include, but are not limited to: 5-fluorouracil (5-FU), azathioprine, cyclophosphamide, antimetabolites (such as Fludarabine), and other antineoplastics such as Etoposide, Doxorubicin, methotrexate, Vincristine, carboplatin, cis-platinum and the taxanes (such as taxol). In a specific example, cisplatin (such as Platinol®) and fluorouracil (such as Adrucil®, Efudex®) are used in combination and in addition to radiation to treat invasive cervical cancer.

Decrease: To reduce the quality, amount, or strength of something.

In one example, a therapy (such as treatment with a $Na^+$, $K^+$-ATPase inhibitor) decreases a cervical dysplasia or cancer (such as the size of a cervical dysplasia or cancer, the number of dysplasias or tumors, the metastasis of a tumor, or combinations thereof), or one or more symptoms associated with cervical dysplasia or cancer, for example as compared to the response in the absence of the therapy. In a particular example, a therapy decreases the size of a cervical dysplasia or cancer, the number of cervical dysplasias or cancers, the metastasis of a cervical cancer, or combinations thereof, subsequent to the therapy, such as a decrease of at least 10%, at least 20%, at least 50%, or even at least 90%. Such decreases can be measured using the methods disclosed herein.

Detect: To determine if an agent is present or absent. In some examples this can further include quantification. For example, antibodies specific for the $Na^+$, $K^+$-ATPase can be used to detect the presence or absence of $Na^+$, $K^+$-ATPase (such as the α- or β-subunit) in a cervical sample, for example by detecting a label associated with the antibody.

Diagnose: The process of identifying a medical condition or disease, for example from the results of one or more diagnostic procedures. In particular examples, includes determining the prognosis of a subject. In a specific example, cervical cancer or cervical dysplasia is diagnosed by detecting $Na^+$, $K^+$-ATPase expression in a cervical sample, wherein increased expression of the $Na^+$, $K^+$-ATPase β-subunit, decreased ratio of α- to β-subunit expression, or combinations thereof, indicates the presence of cervical dysplasia or cancer. For example, can include determining the particular stage of cervical dysplasia or cancer present.

Digitalis: A cardiac glycoside present in the foxglove plant, which significantly reduces the biological activity of the $Na^+$, $K^+$-ATPase, and thus is a $Na^+$, $K^+$-ATPase inhibitor. Examples of digitalis compounds include digoxin, digitoxin, strophanthin and ouabain.

Expression: The process by which the coded information of a gene is converted into an operational, non-operational, or structural part of a cell, such as the synthesis of a protein.

The expression of a nucleic acid molecule can be altered relative to a normal (wild type) nucleic acid molecule. Alterations in gene expression, such as differential expression, includes but is not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard.

Controls or standards for comparison to a sample, for the determination of differential expression, include samples believed to be normal (in that they are not altered for the desired characteristic, for example a sample from a subject who has not had cervical dysplasia or cervical cancer) as well as laboratory values, even though possibly arbitrarily set, keeping in mind that such values can vary from laboratory to laboratory.

Laboratory standards and values may be set based on a known or determined population value and can be supplied in the format of a graph or table that permits comparison of measured, experimentally determined values.

Increase: To make or be greater in the quality, amount, or strength of something. For example, expression of a $Na^+$, $K^+$-ATPase P-subunit protein or nucleic acid molecule in cervical dysplasia and cervical cancer cells is said to be "increased" relative to normal (non-dysplastic or non-cancer cervical cells) when the detected level of β-subunit is at least 2-fold, such as at least 3-fold, at least 4-fold, or at least 10-fold greater in a test cervical sample relative to a normal sample.

Label: An agent capable of detection, for example by ELISA, spectrophotometry, flow cytometry, or microscopy. For example, a label can be attached to a protein or nucleic acid molecule, such as a subunit of the $Na^+,K^+$-ATPAse, thereby permitting detection of the protein or nucleic acid molecule. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998).

$Na^+$, $K^+$-ATPase (sodium, potassium-adenosine triphosphatase): Also referred to in the art as the sodium pump. The $Na^+$, $K^+$-ATPase is a ubiquitous membrane transport enzyme (EC 3.6.3.9) in mammalian cells that is responsible for establishing and maintaining high $K^+$ and low $N^{a+}$ in the cytoplasm required for normal resting membrane potentials and various cellular activities. In the membrane, the $Na^+$, $K^+$-ATPase includes two α and two β-subunits. There are at least four different isoforms of the α- (α1, α2, α3 and α4) and β- (β1, β2, β3, and β4) subunits.

$Na^+$, $K^+$-ATPase inhibitor: An agent capable of significantly reducing the biological activity of the $Na^+$, $K^+$-ATPase. Such an agent can work at the nucleic acid level (for example by decreasing expression of the $Na^+$, $K^+$-ATPase, such as an siRNA molecule), or at the protein level (for example by reducing the activity of the protein). Inhibitors, may, but need not reduce $Na^+$, $K^+$-ATPase biological activity or expression by 100%. For example, therapeutic effects may be observed when the inhibitor decreases $Na^+$, $K^+$-ATPase biological activity or expression by at least 20%, at least 50%, at least 75%, or at least 90%. Exemplary $Na^+$, $K^+$-ATPase inhibitors that act at the protein level are known in the art, and can include cardiac glycosides.

Neoplasm: An abnormal cellular proliferation, which includes benign and malignant tumors, as well as other proliferative disorders. In particular examples a cervical neoplasm includes cervical dysplasia and cervical cancer.

Pharmaceutical agent or drug: A chemical compound or composition capable of inducing a desired therapeutic effect when administered to a subject, alone or in combination with another therapeutic agent(s) or pharmaceutically acceptable carriers. In a particular example, a pharmaceutical agent (such as one that includes a $Na^+$, $K^+$-ATPase inhibitor) treats a cervical dysplasia or cancer, for example by reducing the size of the dysplasia or cancer (such as the volume or reducing the number of dysplasia or cancer cells), reducing metastasis of the cancer, or combinations thereof.

Pharmaceutically Acceptable Carriers: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic agents, such as a $Na^+$, $K^+$-ATPase inhibitor.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate. Exemplary topical carriers include, but are not limited to, those suitable for cervical or vaginal administration.

Reference value: A number or range of numbers representing a particular condition. An experimental value can be compared to the reference value, for example to make a diagnosis or prognosis. For example, a reference value can be a relative or absolute amount (or range) of $Na^+$, $K^+$-ATPase expression (such as α- or β-subunit) expected for a particular cervical condition, such as normal cervical cells, cervical dysplasia (for example a particular stage of dysplasia), or cervical cancer (for example a particular stage of cancer).

Sample: Biological specimens such as samples containing biomolecules, such as nucleic acid molecules, proteins, or both. Exemplary samples are those containing cells or cell lysates from a subject, such as those present in peripheral blood (or a fraction thereof such as serum), urine, saliva, tissue biopsy, cheek swabs, surgical specimen, fine needle aspirates, cervical samples, and autopsy material. In a specific example, a sample is obtained from the cervix (for example a PAP smear), which can include cells from both the outside of the cervix (exocervix, or portio) and the inside of the cervix (endocervix).

Subject: Living multi-cellular vertebrate organisms, a category that includes human and non-human mammals (such as laboratory or veterinary subjects).

Therapeutically effective amount: An amount of an agent that alone, or together with a pharmaceutically acceptable carrier or one or more additional therapeutic agents, induces the desired response. A therapeutic agent, such as a $Na^+$, $K^+$-ATPase inhibitor, is administered in therapeutically effective amounts that stimulate the desired response, for example treatment of cervical dysplasia or cancer.

Effective amounts a therapeutic agent can be determined in many different ways, such as assaying for improvement of a physiological condition of a subject having cervical dysplasia or cancer. Effective amounts also can be determined through various in vitro, in vivo or in situ assays.

Therapeutic agents can be administered in a single dose, or in several doses, for example weekly, monthly, or bimonthly, during a course of treatment. However, the effective amount of can be dependent on the source applied, the subject being treated, the severity and type of the condition being treated, and the manner of administration.

In one example, it is an amount sufficient to partially or completely alleviate symptoms of a cervical dysplasia or cancer in a subject. Treatment can involve only slowing the progression of the cervical dysplasia or cancer temporarily, but can also include halting or reversing the progression of the cervical dysplasia or cancer permanently. For example, a pharmaceutical preparation can decrease one or more symptoms of the cervical dysplasia or cancer (such as the size of the dysplasia or cancer or the number of tumors), for example decrease a symptom by at least 20%, at least 50%, at least 70%, at least 90%, at least 98%, or even at least 100%, as compared to an amount in the absence of the pharmaceutical preparation.

Treating a disease: "Treatment" refers to a therapeutic intervention that ameliorates a sign or symptom of a disease or pathological condition, such a sign or symptom of cervical dysplasia or cervical cancer. Treatment can also induce remission or cure of a condition, such as cervical dysplasia or cervical cancer. In particular examples, treatment includes preventing a disease, for example by inhibiting the full development of a disease, such as preventing development of a cervical cancer from a cervical dysplasia or preventing metastasis of a cervical cancer. Prevention of a disease does not require a total absence of a dysplasia or cancer. For example, a decrease of at least 50% can be sufficient.

Under conditions sufficient for: A phrase that is used to describe any environment that permits the desired activity.

In one example, includes incubating a $Na^+$, $K^+$-ATPase antibody with a cervical sample under conditions that allow the antibody to specifically bind to $Na^+$, $K^+$-ATPase proteins in the sample. In another example, includes contacting one or more $Na^+$, $K^+$-ATPase inhibitors with cervical dysplasia or cervical cancer cells in a subject sufficient to allow the desired activity. In particular examples, the desired activity is decreasing growth or multiplication of such cells, or the invasion of such cells into the cervix, or metastasis of such cells to other organs.

Unit dose: A physically discrete unit containing a predetermined quantity of an active material (such as a $Na^+$, $K^+$-ATPase) calculated to individually or collectively produce a desired effect such as a therapeutic effect. A single unit dose or a plurality of unit doses can be used to provide the desired effect, such as a therapeutic effect.

Overview

The $Na^+$, $K^+$-ATPase has two major functions for maintaining cell functions $Na^+/K^+$ pump and signal transduction. It is shown herein that the expression patterns of $Na^+$, $K^+$-ATPase $\alpha$- and $\beta$1-subunits differed between normal and dysplasia and cancer cervical tissues. For example, increased $Na^+$, $K^+$-ATPase $\alpha$- and $\beta$1-subunit expression was observed in the cervical dysplasia and cervical cancer tissues. In addition, the ratio of the $Na^+$, $K^+$-ATPase $\alpha$- and $\beta$1-subunits was altered between normal and $Na^+$, $K^+$-ATPase $\alpha$- and $\beta$1-subunits. The relative ratio of $Na^+$, $K^+$-ATPase $\alpha$-subunit to $\beta$1-subunit decreased in the cervical dysplasia and cervical cancer tissues relative to the normal cervical samples.

The endocervical mucus glands in the stroma tissue positive for $Na^+$, $K^+$-ATPase $\alpha$ and $\beta$1 subunits were mainly localized below the HPV-induced lesions. In endometrial epithelial cells, insulin-like growth factor I (IGF-I) stimulates $Na^+$, $K^+$-ATPase activity in the endometrial epithelial cells (Deachapunya et al., *J Gen. Physiol.* 114:561-72, 1999). The inventors observed IGF-I immunoreactivity in the endocervical mucus glands of the stroma and IGF-I receptor immunoreactivity in the epithelial cell layer. The inventors also observed insulin-like growth factor binding protein 3 (IGFBP-3) protein accumulation sites and $Na^+/K^+$-ATPase $\beta$1 expression sites in the cervical epithelia cells and cancer cells. This indicates a paracrine regulatory mechanism between the epithelial cell layer and the stroma in the cervical tissue.

Without wishing to be bound to a particular theory, it is proposed that over-expressed IGFBP-3 in the epithelial layer of the cervix due to HPV infection enhances the IGF-I receptor sensitivity. IGF-I secreted from the mucus glands binds to IGF-I receptor in the epithelial layer, and IGF-I binding to the receptor causes signal transduction including an increase in $Na^+$, $K^+$-ATPase and KCC expression and phenotype transformation of HPV-infected cells (cancer development and progression).

Based on these observations, methods of detecting cervical dysplasia or cervical cancer in clinical tissue sections are provided. In addition, methods of treating cervical dysplasia and cervical cancer are provided. For example, inhibitors of the $Na^+$, $K^+$-ATPase (such as a digitalis compound, for example ouabain or digitoxin) can be applied to the cervix (for example in the form of a topical ointment) to treat cervical dysplasia and cervical cancer. Such inhibitors can significantly reduce the expression or biological activity of the $Na^+$, $K^+$-ATPase. In some examples, the $Na^+$, $K^+$-ATPase $\beta$1 subunit is targeted.

Methods of Detecting Cervical Dysplasia and Cervical Cancer

The present disclosure provides methods that can be used to detect a cervical neoplasm, such as a cervical dysplasia or cervical cancer. Detection can include determining whether the cervical dysplasia or cervical cancer is present, grading the cervical dysplasia or cervical cancer (for example determining if it is a CIN I, CIN II, or CIN III cervical dysplasia, or a Stage 0, Stage I (such as Stage IA, IA1, IA2, IB1, IB2), Stage II (such as IIA or IIB), Stage III (such as IIIA or IIIB), or Stage IV (such as IVA or IVB) or cervical cancer), determining the prognosis of a subject found to have cervical dysplasia or cervical cancer, or combinations thereof.

In particular examples, the method includes detecting a $Na^+$, $K^+$-ATPase or subunit thereof (such as an $\alpha$-subunit, $\beta$-subunit, or both) in a cervical sample obtained from the subject, such as detecting $Na^+$, $K^+$-ATPase protein expression or nucleic acid molecule expression. For example, expression of the $\beta$-subunit (such as the $\beta$1-subunit), the $\alpha$-subunit, or both, can be detected. In particular examples, the expression levels are quantitated. Methods of detecting protein or nucleic acid molecule expression are well known.

In particular examples, the presence of a significant increase in expression of a $Na^+$, $K^+$-ATPase (such as the $\beta$-subunit, for example the $\beta$1-subunit), such as at least a 2-fold increase, relative to a level of $Na^+$, $K^+$-ATPase expression in normal cervical tissue (non-cancerous and non-dysplastic), indicates the presence of cervical dysplasia or cervical cancer in the cervical sample obtained from the subject. In specific examples, detection of an at least 2-fold increase (such as at least 3-fold, at least 4-fold, or 2- to 10-fold) in expression of the $Na^+$, $K^+$-ATPase $\beta$1-subunit, relative to such expression in normal cervical tissue, indicates the presence of cervical dysplasia or cervical cancer in the cervical sample obtained from the subject. Exemplary changes are provided in Table 1.

TABLE 1

Exemplary relative values of $Na^+$, $K^+$-ATPase expression

| Tissue | Relative $\beta$1-subunit expression | Relative $\alpha$-subunit to $\beta$1-subunit expression |
| --- | --- | --- |
| Normal Cervical Tissue | 0 | 1 |
| Cervical Dysplasia | at least 2 (such as 2-4) | 0.75 or less (such as 0.75-0.6) |

TABLE 1-continued

Exemplary relative values of $Na^+$, $K^+$-ATPase expression

| Tissue | Relative β1-subunit expression | Relative α-subunit to β1-subunit expression |
| --- | --- | --- |
| Cervical Cancer | at least 5 (such as 5-10) | 0.5 or less (such as 0.5-0.01) |

The detected $Na^+$, $K^+$-ATPase expression can be compared to a reference value or reference sample representing a particular disease or disease-free state (such as normal cervical tissue, cervical dysplasia or cervical cancer, or a particular stage of dysplasia or cancer). For example, the detected level of $Na^+$, $K^+$-ATPase expression in the sample can be compared to a level of $Na^+$, $K^+$-ATPase expression in one or more reference cervical tissue samples or to a reference value representing expected $Na^+$, $K^+$-ATPase expression in a control tissue sample. Exemplary reference samples and values include those representing a known presence, absence, or grade of cervical dysplasia or cervical cancer. For example, if the detected level of $Na^+$, $K^+$-ATPase expression (such as expression of the β-subunit, for example the β1-subunit) is substantially similar to the level of $Na^+$, $K^+$-ATPase expression (such as expression of the β-subunit, for example the β1-subunit) in a particular reference sample or value, this indicates that the subject has that presence, absence or grade of cervical dysplasia or cervical cancer represented by the reference sample or value. In a specific example, if the reference value or sample is normal (non-dysplastic, non-cancerous) cervical cells, a detected increase in $Na^+$, $K^+$-ATPase expression of at least 2-fold (such as at least 3-fold) relative to such a reference value indicates the presence of cervical dysplasia or cervical cancer in the cervical sample obtained from the subject.

In a specific example, detection of the β-subunit (for example the β1-subunit) is performed. If the detected level of β-subunit in the test cervical sample is substantially similar to the level of β-subunit expression in a particular reference sample or value, this indicates that the subject has that presence, absence or grade of cervical dysplasia or cervical cancer represented by the reference sample or value. For example, if the detected relative value of β subunit expression is 50, and the reference value for β-subunit expression is 10 for normal cervical tissue, the reference value for β-subunit expression is 40 for cervical dysplasia, and the reference value for β-subunit expression is 100 for cervical cancer, then it is concluded that the subject has cervical dysplasia. Similar methods can be used to determine whether the subject has normal, dysplasic, or cancerous cervical cells using any $Na^+$, $K^+$-ATPase subunit and the appropriate reference values or samples.

In a specific example, the reference value or sample is normal cervical cells (non-dysplastic, non-cancerous), and expression of the $Na^+$, $K^+$-ATPase β1-subunit is detected, wherein an at least 2-fold (such as at least 3-fold) increased in β1-subunit expression relative to the reference value indicates the presence of cervical dysplasia or cervical cancer in the cervical sample obtained from the subject.

The disclosed method can include detecting both α-subunit and β-subunit $Na^+$, $K^+$-ATPase expression in a cervical tissue sample. For example, the method can include determining the ratio of α- to β-subunit expression, wherein an at least 20% decrease relative to a level of α- to β-subunit expression in normal cervical tissue (non-cancerous and non-dysplastic), indicates the presence of cervical dysplasia or cervical cancer in the cervical sample obtained from the subject. In specific examples, detection of an at least 20%, at least 40%, at least 50%, or at least 75% decrease in ratio of α1- to β1-subunit expression, relative to such expression in normal cervical tissue, indicates the presence of cervical dysplasia or cervical cancer in the cervical sample obtained from the subject.

In some examples, the determined ratio of α- to β-subunit expression is compared to a ratio of α- and β-subunit expression observed in one or more reference values or samples having a known presence, absence or grade of cervical dysplasia or cervical cancer. For example, if the detected ratio of α- and β-subunit expression is substantially similar to the ratio of α- and β-subunit expression in a particular reference sample or value, this indicates that the subject has that presence, absence or grade of cervical dysplasia or cervical cancer represented by the reference sample or value. In a specific example, if the reference value or sample is normal (non-dysplastic, non-cancerous) cervical cells, a detected decrease in the ratio of α- and β-subunit expression (such as a decrease of at least 20% or at least 50%) relative to such a reference value indicates the presence of cervical dysplasia or cervical cancer in the cervical sample obtained from the subject.

The method of detecting cervical dysplasia or cervical cancer can also include determining the localization pattern of the $Na^+$, $K^+$-ATPase (such as the α- or β-subunit) in a cervical sample. The location of either or both of the α- or β-subunits in a cervical tissue sample can be compared to one or more reference values or samples having a known presence, absence or grade of cervical dysplasia or cervical cancer. For example, if the detected $Na^+$, $K^+$-ATPase localization is substantially similar to the $Na^+$, $K^+$-ATPase localization in a particular reference sample or value, this indicates that the subject has that presence, absence or grade of cervical dysplasia or cervical cancer represented by the reference sample or value. In a specific example, if the reference value or sample is normal (non-dysplastic, non-cancerous) cervical cells, a detected $Na^+$, $K^+$-ATPase localization (such as increased localization in the cell membrane, for example relative to basal localization) relative to such a reference value indicates the presence of cervical dysplasia or cervical cancer in the cervical sample obtained from the subject.

DNA replication status is an indication of cell growth rate, particularly in carcinogenesis. $Na^+$, $K^+$-ATPase expression in cervical tissue can indicate cellular physiological status, but does not indicate the status of cell cycle. Therefore, in some examples the method further includes detecting a cell cycle marker, such as histone H3 (for example using histone H3-specific antibodies). Such detection can be used to provide additional information on the ability to diagnose a subject as having a cervical dysplasia or cancer. For example, increased detection of a cell cycle marker relative to normal cervical cells can indicate the presence of increased cell division, such as that occurring in cervical dysplasia or cancer. In some examples, a detectable increase of at least 2-fold more histone H3 or other cell cycle marker (such as at least 5-fold, or at least 20-fold) relative to normal cervical tissue, coupled with one or more of increased β-subunit (such as β1) expression, decreased ratio of α- to β-subunit expression, increased cell membrane staining, or combinations thereof, indicates that the subject has cervical dysplasia or cancer.

Detecting $Na^+$, $K^+$-ATPase Protein Expression

Methods of detecting a protein in a sample are well known in the art. For example, immunoassays and immunocytology methods can be used. However, the disclosure is not limited to particular methods of detection. The availability of antibodies specific for the $Na^+$, $K^+$-ATPase (such as antibodies specific to the α- or β-subunit, such as a particular isoform thereof), facilitate the detection and quantitation of Na+, K+-ATPase proteins. Exemplary commercially available antibodies are shown in Table 2. Exemplary immunoassay methods are presented in Harlow and Lane (*Antibodies, A Laboratory Manual*, CSHL, New York, 1988), Bancroft and Stevens (*Theory and Practice of Histological Techniques*, Churchill Livingstone, 1982) and Ausubel et al (*Current Protocols in Molecular Biology*, John Wiley & Sons, New York, 1998).

TABLE 2

Exemplary Na+, K+-ATPase-specific antibodies

| α-subunit (manufacturer, catalog number) | β-subunit (manufacturer, catalog number) |
| --- | --- |
| α1: Abcam, ab2867; Santa Cruz Biotechnology, Inc., sc-16041; GeneTex, Inc., GTX22872 | β1: Abcam, ab8344; Santa Cruz Biotechnology, Inc., sc-21713 and sc-25709; GeneTex, Inc., GTX30203 and GTX22873 |
| α2: Santa Cruz Biotechnology, Inc., sc-16049; Chemicon, AB9094 | β2: Upstate (Temecula, CA), 06-171 and BD Biosciences Pharmingen (San Diego, CA), 610915 |
| α3: Santa Cruz Biotechnology, Inc., sc-16052 and Upstate 06-172 | β3: BD Biosciences Pharmingen, 610992 |
| | β: Abcam, ab35645; Chemicon, CBL223 |

Generally, the method includes contacting a biological sample obtained from a subject (such as a sample containing cervical cells or proteins isolated from such a sample) with a Na+, K+-ATPase-specific antibody under conditions sufficient for the antibody to specifically bind to Na+, K+-ATPase proteins in the sample, thereby forming Na+, K+-ATPase-antibody complexes. The resulting Na+, K+-ATPase-antibody complexes are then detected using any standard detection system. For example, the Na+, K+-ATPase-antibody can include a label, thereby permitting detection of the complexes. In some examples, the Na+, K+-ATPase-antibody complexes are contacted with an appropriate labeled secondary antibody under conditions sufficient to permit specific binding of the secondary antibody to Na+, K+-ATPase-antibody complexes, thereby forming labeled-Na+, K+-ATPase-antibody complexes. The label associated with the secondary label can then be detected. Similar methods can be used to detect the Na+, K+-ATPase localization pattern in cervical cells obtained from the subject.

Methods for labeling antibodies so that they can be detected are well known. Exemplary labels include fluorophores, such as Cy3, FITC, BODIPY, and Cy5. Methods of detecting labels are known, and include detection using microscopy and flow cytometry.

In some examples, the biological sample includes cervical proteins isolated from a cervical sample. In such examples, any standard immunoassay format (such as ELISA, Western blot, or RIA assay) can be used to measure Na+, K+-ATPase protein levels.

In addition, Na+, K+-ATPase proteins can be detected and quantitated using antibody probe arrays, quantitative spectroscopic methods (for example mass spectrometry, such as surface-enhanced laser desorption/ionization (SELDI)-based mass spectrometry), or combinations thereof.

Detecting Na+, K+-ATPase Nucleic Acid Molecule Expression

Methods of detecting a target nucleic acid molecule (such as RNA or DNA, for example mRNA or cDNA) in a sample are well known in the art. For example, nucleic acid amplification methods (with the appropriate probes and primers), as well as nucleic acid arrays (containing the appropriate probes), can be used. For example, the level of Na+, K+-ATPase gene expression can be determined or even quantitated utilizing methods well known in the art, such as Northern-Blots, RNase protection assays, nucleic acid arrays, quantitative PCR (such as TaqMan assays), dot blot assays, in-situ hybridization, or combinations thereof.

In one example, the method includes contacting nucleic acid molecules (which can be isolated) from a biological sample obtained from a subject (such as a sample containing cervical cells or nucleic acid molecules obtained from such a sample) with a Na+, K+-ATPase-specific nucleic acid probe (such as probe specific for the α- or β-subunit) under conditions sufficient for the probe to specifically bind to Na+, K+-ATPase nucleic acid molecules (such as mRNA molecule)in the sample, thereby forming Na+, K+-ATPase-nucleic acid molecules complexes. The resulting complexes are then detected using any standard detection system, for example by detecting a label on the probe.

In another example, the method includes contacting nucleic acid molecules (which can be isolated) from a biological sample obtained from a subject (such as a sample containing cervical cells or nucleic acid molecules obtained from such a sample) with primers that permit amplification of the Na+, K+-ATPase (such as the α- or β-subunit). The resulting amplicons can be detected, for example by detecting a label on the amplicon. In a specific example, the amplicons are applied to a nucleic acid molecule detection array containing Na+, K+-ATPase-specific nucleic acid probes that can hybridize specifically to the amplicons, under suitable hybridization conditions to form a hybridization complex. The hybridization conditions are selected to permit discrimination between matched and mismatched oligonucleotides. Hybridization conditions can be chosen to correspond to those known to be suitable in standard procedures for hybridization to filters and then optimized for use with the arrays. For example, conditions suitable for hybridization of one type of target (such as a subunit of the Na+, K+-ATPase) are adjusted for the use of other targets (such as a control sequence) for the array. In particular, temperature is controlled to substantially eliminate formation of duplexes between sequences other than exactly complementary Na+, K+-ATPase sequences. A variety of known hybridization solvents can be employed, the choice being dependent on considerations known to one of skill in the art (see U.S. Pat. No. 5,981,185). Detecting a hybridized complex in an array of oligonucleotide probes has been previously described (see U.S. Pat. No. 5,985,567). In one example, detection includes detecting one or more labels present on the oligonucleotides, the sequences obtained from the subject, or both. Detection can further include treating the hybridized complex with a conjugating solution to effect conjugation or coupling of the hybridized complex with the detection label, and treating the conjugated, hybridized complex with a detection reagent. In particular examples, the method further includes quantification, for instance by determining the amount of hybridization.

Methods for labeling nucleic acid molecules so that they can be detected are well known. Examples of such labels include non-radiolabels and radiolabels. Non-radiolabels include, but are not limited to enzymes, chemiluminescent compounds, fluorophores, metal complexes, haptens, colorimetric agents, dyes, or combinations thereof. Radiolabels include, but are not limited to, $^{125}$I and $^{35}$S. Radioactive and fluorescent labeling methods, as well as other methods known in the art, are suitable for use with the present disclosure. In one example, the primers used to amplify the subject's nucleic acids are labeled (such as with biotin, a radiolabel, or a fluorophore). In another example, the amplified nucleic acid samples are end-labeled to form labeled amplified material. For example, amplified nucleic acid molecules can be labeled by including labeled nucleotides in the amplification reactions. In another example, nucleic acid molecules obtained from a subject are labeled, and applied to an array containing oligonucleotides.

Reference Values and Samples

In some examples, the detected $Na^+$, $K^+$-ATPase (such as an α- or β-subunit protein or nucleic acid) can be compared to a reference value (such as a number or range of values) or reference sample (such as an actual biological sample). A comparison to a reference sample or value representing $Na^+$, $K^+$-ATPase expression expected for normal cervical tissue or a particular disease state, such as cervical dysplasia or cervical cancer (or a particular stage thereof), can be used to determine if the subject from whom the sample was obtained has cervical dysplasia or cervical cancer.

In one example, the reference value or sample represents a relative or actual amount of $Na^+$, $K^+$-ATPase α- or β-subunit (or both) expression expected or routinely observed for normal (non-dysplastic, non cancerous) cervical tissue. In another example, the reference value or sample represents a relative or actual amount of $Na^+$, $K^+$-ATPase α- or β-subunit (or both) expression expected or routinely observed for cervical dysplasia or a particular grade thereof (such as CIN I, CIN II, or CIN III). In another example, the reference value or sample represents a relative or actual amount of $Na^+$, $K^+$-ATPase α- or β-subunit (or both) expression expected or routinely observed for cervical cancer or a particular grade thereof (such as Stage 0, Stage I, Stage II, Stage III, or Stage IV, or a substage thereof such as Stage IIA). In some examples, one or more of such reference value or samples are used, such as at least 2, at least 5, at least 10 of such reference values or samples, for example, 1, 2, 3, 4, 5, 6, 7, 8, 9, 10, 11, 12, 13, 14, 15 or 16 of such reference values or samples.

In some examples, the reference sample or value represents a $Na^+$, $K^+$-ATPase localization pattern expected for normal cervical tissue or a particular disease state, such as cervical dysplasia or cervical cancer (or a particular stage thereof). In one example, the reference value or sample represents a relative or actual $Na^+$, $K^+$-ATPase α- or β-subunit (or both) localization expected or routinely observed for normal (non-dysplastic, non cancerous) cervical tissue. In another example, the reference value or sample represents a relative or actual $Na^+$, $K^+$-ATPase α- or β-subunit (or both) localization expected or routinely observed for cervical dysplasia or a particular grade thereof (such as CIN I, CIN II, or CIN III). In another example, the reference value or sample represents a relative or actual $Na^+$, $K^+$-ATPase α- or β-subunit (or both) localization expected or routinely observed for cervical cancer or a particular grade thereof (such as Stage 0, Stage I, Stage II, Stage III, or Stage IV, or a substage thereof such as Stage IIA). In some examples, one or more of such reference value or samples are used, such as at least 2, at least 5, at least 10 of such reference values or samples, for example, 1, 2, 3, 4, 5, 6, 7, 8, 9, 10, 11, 12, 13, 14, 15 or 16 of such reference values or samples.

In some examples, reference values or samples representing $Na^+$, $K^+$-ATPase expression and reference value or samples representing $Na^+$, $K^+$-ATPase localization patterns are used.

Treatment of Cervical Dysplasia and Cervical Cancer

In recognition of the increase in $Na^+$, $K^+$-ATPase β-subunit levels observed in dysplastic cervical tissue and in cervical cancer, a medicament and method for treatment of cervical dysplasia and cervical cancer is provided. In some examples, the subject is first screened to determine if they have cervical dysplasia or cancer, for example using the methods provided herein. Subjects having cervical dysplasia or cancer can be selected for treatment, for example using the treatment methods provided herein.

For example, subjects identified as having at least a 2-fold increase in $Na^+$, $K^+$-ATPase expression in their cervical sample relative to a reference value of $Na^+$, $K^+$-ATPase expression for a cervical sample negative for cervical dysplasia or cervical cancer can be selected for treatment. Exemplary treatments include administration of one or more $Na^+$, $K^+$-ATPase inhibitors, for example to the diseased cervical cells. In some examples, such subjects receive surgery to at least partially remove the cervical dysplasia or cervical cancer cells (such as loop electrosurgical excision procedure (LEEP), cone biopsy, or hysterectomy), radiation therapy, chemotherapy, treatment with one or more $Na^+$, $K^+$-ATPase inhibitors, or combinations thereof.

Compositions

Therapeutic compositions are provided. In particular examples, the therapeutic composition includes one or more $Na^+$, $K^+$-ATPase inhibitors (such as an agent that inhibits the $Na^+$, $K^+$-ATPase β-subunit), and pharmaceutically acceptable carrier. In some examples, such compositions can be used to treat cervical dysplasia or cancer.

$Na^+$, $K^+$-ATPase inhibitors are agents that significantly decrease the biological activity of the $Na^+$, $K^+$-ATPase. Although such a decrease can be a 100% reduction in biological activity, a 100% reduction is not required for the composition to be effective. For example, a $Na^+$, $K^+$-ATPase inhibitor can be an agent that reduces the biological activity of a $Na^+$, $K^+$-ATPase by at least 20%, at least 50%, or at least 90%. Methods of measuring $Na^+$, $K^+$-ATPase biological activity are known in the art, and the disclosure is not limited to particular methods. In one example, the method includes measuring the uptake of $^{86}Rb^+$ as an indicator of $Na^+$, $K^+$-ATPase ion transport activity. For example, cells can be incubated with 1 µCi of $^{86}Rb^+$ as the chloride salt (Amersham Biosciences) per $10^6$ cells, and the reaction stopped after 30 minutes by placing cells on ice with addition of ice-cold phosphate-buffered saline followed by pelleting of the cells. The cell pellets were counted in a counter (Cobra Quantium, Packard), wherein the amount of $^{86}Rb^+$ detected is reflective of $Na^+$, $K^+$-ATPase activity (for example greater amounts of $^{86}Rb^+$ detected indicate greater $Na^+$, $K^+$-ATPase activity). Another method that can be used to determine $Na^+$, $K^+$-ATPase activity is to measure ATPase activity in microsomes using a coupled-enzyme assay (for example see Norby, *Methods Enzymol.* 156: 1169, 1988), wherein the contribution of $Na^+$, $K^+$-ATPase activity to the total ATPase activity can be determined both by testing the sensitivity of the samples to the a $Na^+$, $K^+$-ATPase-specific inhibitor, such as ouabain or oligomycin and by measuring the ATPase activity in a $K^+$-free medium.

In one example, a Na$^+$, K$^+$-ATPase inhibitor is an agent that significantly decreases the biological activity of the Na$^+$, K$^+$-ATPase protein. For example, the Na$^+$, K$^+$-ATPase inhibitor can be a cardiac glycoside, such as a cardiac glycoside isolated from a plant or animal. Examples of cardiac glycosides include oubain and g/k/e-strophanthin (from *Strophanthus*), digitalis, digoxin and digitoxin (from *Digitalis lanata* and *Digitalis purpurea*), proscillaridine A (from *Scilla maritima*), vitexin and rutin (from *Crataegus*), as well as cardiac glycosides from *Adonis vernalis, Adonis aestivalis, Ammi visnaga, Acokanthera oblongifolia*, and *Convallaria*, as well as frog (such as bufalin, marinobufagenin and bufadienolides). A glycolipoprotein fraction prepared from *Leptospira interrogans* has also been shown to have Na$^+$, K$^+$-ATPase inhibitory activity. In a specific example, the Na$^+$, K$^+$-ATPase inhibitor is a digitalis compound.

In one example, the cardiac glycoside is present in the composition at a therapeutically effective amount, such as an amount that reduces Na$^+$, K$^+$-ATPase biological activity in cervical dysplasia or cancer cells. For example, the cardiac glycoside can be present in the composition in an amount that reduces growth of or kills cervical dysplasia or cancer cells. In a specific example, the cardiac glycoside is present in the composition at a concentration of at least 0.01 mg per gram by weight of the composition, such as at least 0.1 mg, at least 0.25 mg, at least 0.5 mg, or at least 5 mg per gram by weight of the composition, such as 0.01 mg to 0.5 mg or 0.01 mg to 10 mg per gram by weight of the composition.

In one example, a Na$^+$, K$^+$-ATPase inhibitor is an agent that significantly decreases expression of the Na$^+$, K$^+$-ATPase. Methods of inhibiting expression in vivo are known in the art, and can include inhibitory RNA (RNAi) molecules, such as siRNA, mRNA, and short hairpin (sh) RNA molecules. In a specific example, the inhibitor significantly decreases expression of the Na$^+$, K$^+$-ATPase β-subunit. Based on the public availability of Na$^+$, K$^+$-ATPase nucleic acid molecules from numerous species (for example see GenBank Accession Nos. AH002617, M30309, U16799, X03747 and NM_001677), RNAi molecules can be generated using routine methods in the art, such as RNAi molecules 20-30 nucleotides in length, such as about 27 nucleotides. Exemplary Na$^+$, K$^+$-ATPase RNAi molecules are provided in US Publication No. 20060172965 and 20060234970. Na$^+$, K$^+$-ATPase RNAi molecules are administered in therapeutically effective amounts, for example to the vagina or cervix. In particular examples, a therapeutic composition includes 0.1% to 99% by weight of the RNAi. Generally, a therapeutically effective amount of the RNAi results in an extracellular concentration at the surface of the target cervical cell (such as a neoplastic cells, for example a dysplastic or cancerous cell) of at least 100 pM, at least 1 nM, or at least 100 nm, for example 100 pM to 100 nM, 1 nM to 50 nM, 5 nM to 10 nM, or 100 pM to 25 nM.

The compositions provided herein can be in the form of an ointment, cream, emulsion, lotion, gel, solid, solution, suspension, foam or liposomal composition; such as a formulation suitable for vaginal or cervical delivery. The pH of the compositions that includes a Na$^+$, K$^+$-ATPase can be about pH 4-9, such as pH 4.5 to pH 7.4. In one example, the therapeutic composition is contained within a vaginal ring, tampon, suppository, sponge, pillow, puff, or osmotic pump system.

Pharmaceutically acceptable carriers include agents that permit delivery of one or more therapeutic agents, such as a Na$^+$, K$^+$-ATPase inhibitor. Pharmaceutically acceptable carriers that can be used are known to those skilled in this art; for example, see Remington's Pharmaceutical Sciences, 18th Ed. (Easton, Pa.: Mack Publishing Company, 1990). In a specific example, the pharmaceutically acceptable carrier is a topical carrier, such as a carrier that is suitable for administration of the composition to cervical tissue in vivo. Topical carriers are known in the art, and include any of those used as a basis for ointments, lotions, creams, salves, aerosols, suppositories, gels and the like, such as those suitable for vaginal or cervical administration.

Suitable carriers for use herein include water, silicone, waxes, petroleum jelly, polyethylene glycol (such as polyethylene glycol-1000 (PEG-1000)), propylene glycol, liposomes, sugars (such as mannitol and lactose), ointment bases; conventional ophthalmic vehicles; creams; and gels. Additional pharmaceutically acceptable carriers that can be used are provided in U.S. Pat. Nos: 6,699,494; 6,306,841; 5,814,338 and US Publication Nos. 2005/0129736 and 2006/0205679.

If desired, the disclosed composition or portion thereof (such as the carrier) can be sterilized or mixed with auxiliary agents, for example thixotropes, stabilizers, wetting agents, and the like.

The disclosed pharmaceutical compositions can be formed by dispersing the finely divided or dissolved Na$^+$, K$^+$-ATPase inhibitor uniformly throughout the vehicle or base using conventional techniques, for example by a levigating the agent with a small quantity of the base to form a concentrate, which is then diluted geometrically with further base. Alternatively, a mechanical mixer can be used. Creams, lotions and emulsions can be formed by way of a two-phase heat system, wherein oil-phase ingredients are combined under heat to provide a liquified, uniform system. For example, the aqueous-phase ingredients are separately combined using heat. The oil and aqueous phases are then added together with constant agitation and allowed to cool. At this point, concentrated agents can be added as a slurry. Volatile or aromatic materials can be added after the emulsion has sufficiently cooled. Preparation of such pharmaceutical compositions is within the general skill of the art.

The Na$^+$, K$^+$-ATPase inhibitor can also be incorporated into a gel formulation using methods known in the art. Two-phase gel systems generally include a suspension or network of small, discrete particles interpenetrated by a liquid to provide a dispersed phase and a liquid phase. Single-phase gel systems are formed by distributing organic macromolecules uniformly throughout a liquid such that there are no apparent boundaries between the dispersed and liquid phases. Suitable gelling agents include synthetic macromolecules (such as Carbomers, polyvinyl alcohols and polyoxyethylene-polyoxypropylene copolymers), gums such as tragacanth, as well as sodium alginate, gelatin, methylcellulose, sodium carboxymethylcellulose, methylhydroxyethyl cellulose and hydroxyethyl cellulose. To prepare a uniform gel, dispersing agents such as alcohol or glycerin can be added, or the gelling agent can be dispersed by trituration, mechanical mixing or stirring, or combinations thereof.

Liposomes can be used to prepare a composition that includes a Na$^+$, K$^+$-ATPase inhibitor. Generally, liposome formulations are used for poorly soluble or insoluble pharmaceutical agents. Liposomal preparations that can be used include cationic (positively charged), anionic (negatively charged) and neutral preparations. Cationic liposomes (such as, N[1-2,3-dioleyloxy)propyl]-N,N,N-triethylammonium ("DOTMA"), available under the tradename Lipofectin (GIBCO BRL, Grand Island, N.Y.)) and anionic and neutral liposomes are readily available or can be easily prepared using readily available materials (such as phosphatidyl choline, cholesterol phosphatidyl ethanolamine, dioleoylphosphatidyl choline ("DOPC"), dioleoylphosphatidyl glycerol ("DOPG"), and dioleoylphoshatidyl ethanolamine ("DOPE")). These materials can also be mixed with DOTMA in appropriate ratios. Methods for making liposomes using these materials are well known in the art.

Methods

The present disclosure also provides methods for treating cervical dysplasia or cervical cancer in a subject, such as a human female subject. In particular examples, the method includes administering a therapeutically effective amount of one or more $Na^+$, $K^+$-ATPase inhibitors to a subject having cervical dysplasia or cancer under conditions that permit treatment of the cervical dysplasia or cancer. Exemplary therapeutic compositions are provided above.

For example, the $Na^+$, $K^+$-ATPase inhibitor can be administered in an amount sufficient to significantly decrease $Na^+$, $K^+$-ATPase biological activity in cells of the cervix, such as dysplastic or cancer cells. In some examples, $Na^+$, $K^+$-ATPase biological activity in cells of the cervix (such as the diseased dysplastic or cancerous cells) is decreased by at least 50%, such as at least 95%. In some examples, administration of a therapeutically effective amount of a $Na^+$, $K^+$-ATPase inhibitor to the cervix reduces the number or size of diseased cervical cells by at least 20%, at least 40%, at least 50%, at least 80%, such as at least 95%.

In some examples, treatment of a cervical dysplasia prevents or delays development of cervical cancer, reduces the stage or grade of dysplasia or cancer (for example CIN III to CIN II or I, or Stage IIIA to a Stage IIA or Stage I or Stage 0), or combinations thereof. For example, the method can be used to treat cervical dysplasia prior to its progression to cancer.

Methods of administration are known in the art. In one example, the therapeutic composition containing one or more $Na^+$, $K^+$-ATPase inhibitor is administered directly to the cervix. For example, the epithelial layer of the cervix can be contacted with a therapeutically effective amount of a $Na^+$, $K^+$-ATPase inhibitor (such as a digitalis compound), thereby decreasing or reversing molecular changes associated progression from dypslasia to cancer or increasing the grade of dysplasia or cancer. Higher concentrations and longer periods of contact can be used to reach and treat invading cancer cells below the epithelial layer, or to reach and treat endocervical glands located below the epithelial layer in dysplastic cervical tissues. In another example, the therapeutic composition containing one or more $Na^+$, $K^+$-ATPase inhibitors is administered vaginally, thereby permitting the composition to reach the diseased cervical cells.

In a specific example, the therapeutic composition containing one or more $Na^+$, $K^+$-ATPase inhibitors is administered to the subject at a dose of at least 0.001 μg/kg of subject, for example at least 0.01 μg/kg, at least 0.1 μg/kg, such as 0.001 μg/kg to 1 μg/kg. The therapeutic composition can be applied in a single unit dose or multiple doses over time, such as daily, weekly, or monthly over a period of time, such as at least one month, at least 6-months, or at least 12-months.

EXAMPLE 1

$Na^+$, $K^+$-ATPase Expression in Cervical Dysplasia and Cervical Cancer

This example describes methods used to compare $Na^+$, $K^+$-ATPase expression in normal, cervical dysplasia, and cervical cancer samples. Although particular detection methods are provided, one skilled in the art will appreciate that other antibodies and other immunohistochemical methods can be used.

Monoclonal anti-$Na^+$, $K^+$-ATPase CL subunit (clone M7-PB-E9) and β1 subunit (clone M17-P5-F11) antibodies (Sigma-Aldrich, Inc., St. Louis, Mo.) were used to detect the α and β1 subunits of the $Na^+$, $K^+$-ATPase, respectively, in cervical tissue samples (namely normal, low grade, high grade, and cancer cases), using a BenchMark XT automated slide stainer (Ventana Medical Systems, Inc., Tucson, Ariz.). The signal for $Na^+$, $K^+$-ATPase α and β1 was visualized with iVIEW DAB (Ventana Medical Systems, Inc.) and tissue sections were counterstained with Hematoxylin II and Bluing Reagent. The specificity of $Na^+$, $K^+$-ATPase α and β1 immunostaining was confirmed with tissue microarray slides containing normal and cancer tissues (Super Bio Chips, Korea).

In general, tissue sections on the tissue microarray slides showed both $Na^+$, $K^+$-ATPase α and β1 subunits in the same cell populations. However, the cell membrane staining patterns for $Na^+$, $K^+$-ATPase α and β1 subunits were different among different tissue types. For example, kidney sections showed the basal and lateral cell surface staining while the small intestine showed mainly the lateral cell surface staining.

$Na^+$, $K^+$-ATPase α and β1 subunits were visualized in the cervical tissue sections. $Na^+$, $K^+$-ATPase a subunit was localized at the basal layer of cervical epithelial layers of the normal cervical tissues (FIG. 1A). The first cell layer next to the stroma tissue showed strong cytoplasmic staining $Na^+$, $K^+$-ATPase α subunit while adjacent a few cell layers toward epithelial surface showed cell membrane staining. However, normal cervical tissues were absent for the $Na^+$, $K^+$-ATPase β1 subunit (FIG. 1B), though the levels of $Na^+$, $K^+$-ATPase β1 subunit might be too low to permit immunohistochemical detection, or a different β subunit (such as β2 and/or β3), may be expressed.

The lesion of all low grade (FIG. 1C) and high grade (FIG. 1E) dysplasia clinical cases showed membrane staining of the $Na^+$, $K^+$-ATPase a subunit. However, low grade (FIG. 1D) and high grade (FIG. 1F) dysplasia clinical samples also demonstrated expression of the $Na^+$, $K^+$-ATPase β1 subunit in the membrane.

Eight out of eight cancer cases were positive for the $Na^+$, $K^+$-ATPase α (FIG. 1G) and β1 (FIG. 1H) subunits. However, the ratio of expression levels for the $Na^+$, $K^+$-ATPase α- and β1-subunits was different in the cancer cell populations (as compared to the dysplasias and the normal tissues). Thus, the expression of the $Na^+$, $K^+$-ATPase α and β1 subunits might be regulated by different mechanisms in the cervical epithelial layer and cancer. Also, endocervical mucus glands were observed under neath of the lesions in the stroma tissue of the dysplastic tissue samples (FIGS. 2C and 2D) but rarely in normal tissue (FIGS. 2A and 2B), and the glands also showed increased levels of the $Na^+$, $K^+$-ATPase α and β1 subunits, especially around the periphery of the glands (FIGS. 2C and 2D).

EXAMPLE 2

Telomere and Centromere Patterns in Cervical Dysplasia

This example describes methods used to visualize chromosomal DNA and compare $Na^+$, $K^+$-ATPase expression in cervical dysplasia samples. Although particular detection methods are provided, one skilled in the art will appreciate that other staining and detection methods can be used.

Telomere and centromere (which serves as DNA positive control) specific oligoprobes were used for in situ hybridization to visualizing chromosomal DNA sequences in cervical tissue samples. Telomere and centromere in situ hybridization applications were optimized on a BenchMark XT instrument by modifying established HPV in situ hybridization protocols. The signal for telomeric and centromeric chromosomal DNA was detected with iVIEW Blue Plus and counterstained with Red Counterstain II. $Na^+$, $K^+$-ATPase β-subunit expression was detected as described in Example 1.

As shown in FIGS. 3A-F, dysplastic cervical tissue samples having different levels of telomeric shortening, and as telomeric shortening occurs, there is a corresponding increase in the level of $Na^+$, $K^+$-ATPase β-subunit expressed in the sample. FIGS. 3A and 3D are positive controls indicating the presence of chromosomal DNA in the samples, FIGS. 3B and 3E show the differing levels of telomeric DNA in two cases of dysplasia (less signal indicating shorter telomeric regions), and FIGS. 3C and 3F show corresponding levels of $Na^+$, $K^+$-ATPase β-subunit expression.

EXAMPLE 3

Topical Medicament and Method for Treating Cervical Dysplasia or Cancer

This example describes compositions that include a $Na^+$, $K^+$-ATPase inhibitor, as well as methods of using such a composition to treat cervical dysplasia or cancer. Although particular exemplary $Na^+$, $K^+$-ATPase inhibitors and methods of administration are provided, the disclosure is not limited to such agents and methods.

As described in the Examples above, there is an increase in $Na^+$, $K^+$-ATPase β-subunit expression observed in dysplastic cervical tissue and in cervical cancer. Based on these observations, a therapeutic composition and method for treatment of cervical dysplasia and cervical cancer are provided.

The therapeutic composition includes one or more $Na^+$, $K^+$-ATPase inhibitors, such as an agent that inhibits the activity or expression of the $Na^+$, $K^+$-ATPase β-subunit (such as the β1-subunit). In a specific example, the $Na^+$, $K^+$-ATPase inhibitor includes a digitalis compound and a pharmaceutically acceptable topical carrier. In a specific example, the digitalis compound is digoxin, digitoxin, or combinations thereof, for example in 0.01 digitalis mg per gram by weight of the composition, such as at least 0.1 mg, at least 0.25 mg, at least 0.5 mg, or at least 5 mg per gram by weight of the composition, such as 0.01 mg to 0.5 mg or 0.01 mg to 10 mg per gram by weight of the composition.

In a particular embodiment, the medicament and method can be used specifically for treatment of cervical dysplasia prior to its progression to cancer. By contacting the epithelial layer (where β-subunit expression levels increase first) with a digitalis compound, the molecular changes associated progression from dypslasia to cancer may be halted or reversed. Higher concentrations and longer periods of contact may be useful for reaching and treating invading cancer cells below the epithelial layer or for endocervical glands located below the epithelial layer in dysplastic cervical tissues.

The digitalis compound can be added to any pharmaceutically acceptable topical carrier to prepare the medicament. The topical carrier can be any of those well-known for use in the pharmaceutical, cosmetic, and medical arts as a basis for ointments, lotions, creams, salves, aerosols, suppositories, gels and the like. If desired, these may be sterilized or mixed with auxiliary agents, e.g., thixotropes, stabilizers, wetting agents, and the like. Examples of vehicles for non-sprayable topical preparations include ointment bases, e.g., polyethylene glycol-1000 (PEG-1000); conventional ophthalmic vehicles; creams; and gels, as well as petroleum jelly and the like.

In view of the many possible embodiments to which the principles of the disclosure can be applied, it should be recognized that the illustrated example are only examples of the disclosure and should not be taken as limiting the scope of the invention, Rather, the scope of the invention is defined by the following claims. We therefore claim as our invention all that comes within the scope and spirit of these claims.

We claim:

1. A method for detecting cervical dysplasia or cervical cancer in a subject, comprising:
    detecting $Na^+$, $K^+$-ATPase expression in a cervical sample obtained from the subject, wherein an increase in expression of at least 2-fold relative to a reference value of $Na^+$, $K^+$-ATPase expression for a cervical sample negative for cervical dysplasia or cervical cancer indicates the presence of cervical dysplasia or cervical cancer in the cervical sample obtained from the subject.

2. The method of claim 1, wherein detecting $Na^+$, $K^+$-ATPase expression comprises detecting $Na^+$, $K^+$-ATPase protein expression.

3. The method of claim 2, wherein detecting $Na^+$, $K^+$-ATPase protein expression comprises:
    contacting the cervical sample with a $Na^+$, $K^+$-ATPase-specific antibody under conditions sufficient for binding of the antibody to $Na^+$, $K^+$-ATPase proteins in the sample, thereby forming $Na^+$, $K^+$-ATPase-antibody complexes; and
    detecting the $Na^+$, $K^+$-ATPase-antibody complexes.

4. The method of claim 3, wherein detecting the $Na^+$, $K^+$-ATPase-antibody complexes comprises:
    contacting the $Na^+$, $K^+$-ATPase-antibody complexes with a secondary antibody comprising a label under conditions sufficient for binding of the secondary antibody to $Na^+$, $K^+$-ATPase-antibody complexes, thereby forming labeled- $Na^+$, $K^+$-ATPase-antibody complexes; and
    detecting the label.

5. The method of claim 2, wherein detecting $Na^+$, $K^+$-ATPase protein expression comprises detecting the $Na^+$, $K^+$-ATPase protein using microscopy or flow cyotometry.

6. The method of claim 1, wherein detecting $Na^+$, $K^+$-ATPase expression comprises detecting $Na^+$, $K^+$-ATPase nucleic acid molecule expression.

7. The method of claim 6, wherein detecting $Na^+$, $K^+$-ATPase nucleic acid molecule expression comprises detecting $Na^+$, $K^+$-ATPase mRNA expression.

8. The method of claim 7, wherein PCR is used to detect $Na^+$, $K^+$-ATPase mRNA expression.

9. The method of claim 1, wherein detecting $Na^+$, $K^+$-ATPase expression comprises quantitating $Na^+$, $K^+$-ATPase expression.

10. The method of claim 1, wherein the reference value further comprises a second reference value of $Na^+$, $K^+$-ATPase expression for a cervical sample positive for cervical dysplasia or cervical cancer, wherein an amount of $Na^+$, $K^+$-ATPase expression substantially similar to an amount of $Na^+$, $K^+$-ATPase expression in the second reference value indicates the presence of cervical dysplasia or cervical cancer in the cervical sample obtained from the subject.

11. The method of claim 1, wherein detecting $Na^+$, $K^+$-ATPase expression comprises detecting $Na^+$, $K^+$-ATPase β subunit expression.

12. The method of claim 1, wherein detecting $Na^+$, $K^+$-ATPase expression further comprises detecting $Na^+$, $K^+$-ATPase α-subunit expression.

13. The method of claim 12, further comprising determining a ratio of α- to β-subunit expression, wherein an at least 20% decrease in the ratio of α- to β-subunit expression relative to a reference value of α- to β-subunit expression for a cervical sample negative for cervical dysplasia or cervical cancer indicates the presence of cervical dysplasia or cervical cancer in the cervical sample obtained from the subject.

14. The method of claim 11, further comprising comparing the ratio of α- to β-subunit expression to a reference value or reference sample, wherein a ratio of α- to β-subunit expression observed in the cervical tissue sample that is substantially similar to a ratio of α- to β-subunit expression observed in a particular reference value or reference sample indicates that the subject has that particular presence, absence or grade of cervical dysplasia or cervical cancer of the reference value or reference sample.

15. The method of claim 1, further comprising:
determining $Na^+$, $K^+$-ATPase localization in cervical cells present in the cervical sample; and,
comparing the $Na^+$, $K^+$-ATPase localization to reference $Na^+$, $K^+$-ATPase localization, wherein $Na^+$, $K^+$-ATPase localization substantially similar to $Na^+$, $K^+$-ATPase localization in the reference indicates that the subject has the presence, absence or grade of cervical dysplasia or cervical cancer of the reference.

16. The method of claim 1, further comprising:
detecting histone H3 in cervical cells present in the cervical sample; and,
comparing histone H3 expression to a reference histone H3 expression, wherein histone H3 expression substantially similar relative to histone H3 expression of the reference indicates that the subject has the presence, absence or grade of cervical dysplasia or cervical cancer of the reference.

17. The method of claim 1, further comprising:
selecting subjects having at least a 2-fold increase in $Na^+$, $K^+$-ATPase expression relative to a reference value of $Na^+$, $K^+$-ATPase expression for a cervical sample negative for cervical dysplasia or cervical cancer for treatment for the cervical dysplasia or cervical cancer.

18. The method of claim 17, further comprising:
administering to the subject a therapeutically effective amount of one or more $Na^+$, $K^+$-ATPase inhibitors to cervical cells.

19. The method of claim 18, wherein the one or more $Na^+$, $K^+$-ATPase inhibitors comprises digitalis.

20. The method of claim 17, further comprising:
resecting cervical dysplasia cells or cervical cancer cells from the subject, administering a therapeutic amount of a chemotherapeutic agent to the subject, administering a therapeutic amount of a radiotherapeutic agent to the subject, or combinations thereof.

21. The method of claim 1, wherein the increase in expression relative to the reference value is at least 3-fold.

22. The method of claim 1, wherein the increase in expression relative to the reference value is 2-fold to 10-fold.

23. The method of claim 1, wherein the increase in expression relative to the reference value is 2-fold.

24. The method of claim 1, wherein the subject is a human female subject.

* * * * *

UNITED STATES PATENT AND TRADEMARK OFFICE
CERTIFICATE OF CORRECTION

PATENT NO.       : 7,851,145 B2
APPLICATION NO.  : 12/096075
DATED            : December 14, 2010
INVENTOR(S)      : Nitta et al.

It is certified that error appears in the above-identified patent and that said Letters Patent is hereby corrected as shown below:

In the Specification:

Column 1, line 64, "subject For" should read --subject. For--

Column 3, line 38, "(A, C, E, G) a and" should read --(A, C, E, G) α and--

Column 3, line 42, "$Na^+$, $K^+$-ATPase a subunit," should read --$Na^+$, $K^+$-ATPase α subunit,--

Column 14, lines 2 and 3, "$Na^+$, $K^+$-AT-Pase" should read --$Na^+$, $K^+$-ATPase--

Column 20, lines 4 and 5, "CL subunit (clone M7-PB-E9)" should read --α subunit (clone M7-PB-E9)--

Column 20, line 39, "$Na^+$, $K^+$-ATPase a subunit." should read --$Na^+$, $K^+$-ATPase α subunit.--

In the Claims:

Column 22, claim 2, lines 23 and 24, "$Na^+$, $K^+$-AT-Pase" should read --$Na^+$, $K^+$-ATPase--

Column 22, claim 3, lines 26 and 27, "$Na^+$, $K^+$-AT-Pase" should read --$Na^+$, $K^+$-ATPase--

Column 22, claim 5, lines 42 and 43 and 43 and 44, "$Na^+$, $K^+$-AT-Pase" should read --$Na^+$, $K^+$-ATPase--

Column 22, claim 6, lines 45 and 46, "$Na^+$, $K^+$-AT-Pase" should read --$Na^+$, $K^+$-ATPase--

Column 22, claim 7, lines 48 and 49, "$Na^+$, $K^+$-AT-Pase" should read --$Na^+$, $K^+$-ATPase--

Column 22, claim 9, lines 54 and 55, "$Na^+$, $K^+$-AT-Pase" should read --$Na^+$, $K^+$-ATPase--

Signed and Sealed this
Twenty-first Day of June, 2011

David J. Kappos
*Director of the United States Patent and Trademark Office*

Column 22, claim 10, lines 58 and 59, "Na$^+$, K$^+$-AT-Pase" should read --Na$^+$, K$^+$-ATPase--

Column 22, claim 11, lines 65 and 66, "Na$^+$, K$^+$-AT-Pase" should read --Na$^+$, K$^+$-ATPase--

Column 23, claim 12, lines 1 and 2, "Na$^+$, K$^+$-AT-Pase" should read --Na$^+$, K$^+$-ATPase--